(12) United States Patent
Dahan et al.

(10) Patent No.: US 9,164,083 B2
(45) Date of Patent: Oct. 20, 2015

(54) MICROFLUIDIC SYSTEM FOR CONTROLLING THE CONCENTRATION OF MOLECULES FOR STIMULATING A TARGET

(75) Inventors: Maxime Dahan, Saint Germain en Laye (FR); Mathieu Morel, Paris (FR); Jean-Christophe Galas, Marcoussis (FR); Vincent Studer, Bordeaux (FR); Denis Bartolo, Lyons (FR)

(73) Assignees: Centre National de la Recherche Scientifique-CNRS, Paris (FR); Ecole Normale Supérieure, Paris (FR); Univerité Pierre et Marie Curie (Paris 6), Paris (FR); Fonds de l'ESPCI-Georges Charpak, Paris (FR); Université Bordeaux Segalen, Bordeaux (FR)

( * ) Notice: Subject to any disclaimer, the term of this patent is extended or adjusted under 35 U.S.C. 154(b) by 34 days.

(21) Appl. No.: 14/113,136

(22) PCT Filed: Apr. 20, 2012

(86) PCT No.: PCT/IB2012/052009
§ 371 (c)(1),
(2), (4) Date: Jan. 8, 2014

(87) PCT Pub. No.: WO2012/143908
PCT Pub. Date: Oct. 26, 2012

(65) Prior Publication Data
US 2014/0113366 A1 Apr. 24, 2014

(30) Foreign Application Priority Data

Apr. 22, 2011 (FR) ...................................... 11 53496

(51) Int. Cl.
*G01N 33/50* (2006.01)
*G01N 21/63* (2006.01)
(Continued)

(52) U.S. Cl.
CPC ...... *G01N 33/5008* (2013.01); *B01L 3/502761* (2013.01); *C12M 23/16* (2013.01);
(Continued)

(58) Field of Classification Search
None
See application file for complete search history.

(56) References Cited

U.S. PATENT DOCUMENTS

| 7,374,906 B2 | 5/2008 | Kirk et al. | |
|---|---|---|---|
| 2004/0142411 A1* | 7/2004 | Kirk et al. | 435/33 |

(Continued)

FOREIGN PATENT DOCUMENTS

| WO | 2007/106451 A2 | 9/2007 |
|---|---|---|
| WO | 2008/009803 A2 | 1/2008 |

(Continued)

OTHER PUBLICATIONS

International Search Report for corresponding International Application No. PCT/IB2012/052009, mailed Aug. 1, 2012 (4 pages).
(Continued)

*Primary Examiner* — Jennifer Wecker
(74) *Attorney, Agent, or Firm* — Osha Liang LLP (57) ABSTRACT

The invention relates to a microfluidic system for controlling a card for the concentration of molecules capable of stimulating a target, for example formed by an assembly of living cells, characterized in that the system comprises a microfluidic device (1) comprising: n≥1 microfluidic channel(s) (4, 40), the or each channel being provided with at least one inlet orifice for at least one fluid and with at least one outlet orifice for this fluid; n≥2 openings (47, 470) formed in the microfluidic channel or distributed in the various microfluidic channels, said openings being arranged in one and the same plane so that they form a network having at least one dimension in this plane, the numbers n of microfluidic channel(s) and n of openings being linked by the relationship (I) with 1≤i≤n and n the number of openings for the channel c; at least one microporous membrane (5) covering the network of openings, the target being intended to be positioned on the side of the membrane which is opposite the microfluidic channel(s); one or more fluid feed means for feeding the or each microfluidic channel with fluid, at least one of these fluids comprising molecules for stimulating the target.

18 Claims, 6 Drawing Sheets

(51) Int. Cl.
  *B81B 1/00*    (2006.01)
  *B01L 3/00*    (2006.01)
  *C12M 3/06*    (2006.01)

(52) U.S. Cl.
  CPC ...... *B01J2219/00639* (2013.01); *B01L 3/5027* (2013.01); *B01L 3/502715* (2013.01); *B01L 3/502753* (2013.01); *B01L 2200/027* (2013.01); *B01L 2200/0647* (2013.01); *B01L 2200/0652* (2013.01); *B01L 2300/0627* (2013.01); *B01L 2300/0681* (2013.01); *B01L 2300/087* (2013.01); *B01L 2300/0816* (2013.01); *B01L 2300/0848* (2013.01); *B01L 2300/0851* (2013.01); *B01L 2300/163* (2013.01)

(56) References Cited

U.S. PATENT DOCUMENTS

| | | | |
|---|---|---|---|
| 2005/0148064 A1* | 7/2005 | Yamakawa et al. | 435/287.2 |
| 2006/0199260 A1 | 9/2006 | Zhang et al. | |
| 2007/0054349 A1* | 3/2007 | Hickey | 435/32 |
| 2009/0250130 A1 | 10/2009 | Studer et al. | |
| 2010/0025567 A1* | 2/2010 | Lueerssen | 250/205 |
| 2010/0197008 A1* | 8/2010 | Handique et al. | 435/325 |
| 2010/0294811 A1* | 11/2010 | Akechi et al. | 222/420 |
| 2011/0020179 A1* | 1/2011 | Yue et al. | 422/63 |
| 2013/0068310 A1* | 3/2013 | Sip et al. | 137/1 |
| 2013/0095519 A1* | 4/2013 | Backman et al. | 435/34 |

FOREIGN PATENT DOCUMENTS

| | | |
|---|---|---|
| WO | 2008/028241 A1 | 3/2008 |
| WO | 2010/013016 A2 | 2/2010 |

OTHER PUBLICATIONS

Written Opinion for corresponding International Application No. PCT/IB2012/052009, mailed Aug. 1, 2012 (6 pages).

R. L. Smith et al., "Microfluidic device for the combinatorial application and maintenance of dynamically imposed diffusional gradients"; Microfluid Nanofluid (2010) 9:613-622; published Feb. 9, 2010 (10 pages).

* cited by examiner

Fig.6
(Cross section A-A)

Fig.8 (Plane P)

MICROFLUIDIC SYSTEM FOR CONTROLLING THE CONCENTRATION OF MOLECULES FOR STIMULATING A TARGET

The present invention relates to the field of microfluidics.

Microfluidics implements systems of micrometric dimensions, the size of which is generally between a few tens and a few hundreds of microns.

These systems have applications in many fields such as cell diagnostic testing, the development of medicines, fundamental biology or cosmetology.

In these fields, there is an increasingly demand for microfluidic systems for quantitatively determining the response of living cells to certain molecules and, particularly, the response to a spatially and temporally controlled concentration map.

For example, the response of cancerous cells to molecules used for chemotherapy may have to be measured. To accurately determine this response, it is necessary to exert control on the application of the molecules which will generate this response. This control may relate to the quantity of molecules interacting with the cancerous cells, the concentration map of the molecules to which the cancerous cells are subjected, the trend over time of the quantity of these molecules and/or of the concentration map of these molecules applied to the cancerous cells, etc.

In the cosmetology field, microfluidic systems can be used for testing the toxicity of certain molecules on living cells and/or cell tissues. Control of the quantity of molecules, possibly toxic, administered to the cells and the manner in which these molecules are administered is necessary to determine the toxicity threshold.

An example of a microfluidic system that is widely used to stimulate living cells is presented in the document U.S. Pat. No. 7,374,906. This microfluidic system notably makes it possible to subject the living cells to a molecule concentration gradient, the map of which here has a linear profile that is stable in time.

A major drawback with this type of microfluidic system is that the living cells are subjected to a flow that generates shearing forces that disturb them. This shearing is particularly problematic when seeking to study the chemotactic response of the growth cone of nerve cells. In practice, the flow generates shear stresses which modify the response of the target cells in the best case, or which even cause the death or tearing away of the cells.

The physiological behavior of the living cells that are thus studied is disturbed with the system disclosed in this document.

Solutions have therefore been proposed for subjecting the living cells to a molecule concentration map and/or to combinations of several different molecule concentration maps, without them being disturbed by a flow.

Such a microfluidic system is, for example, presented in the article "*Microfluidic device for the combinatorial application and maintenance of dynamically imposed diffusional gradients*", R. L. Smith & al., (2010) 9: 613-622.

This microfluidic system comprises a microfluidic device 100 and means (not represented) for supplying the device with fluids.

Figure 1:
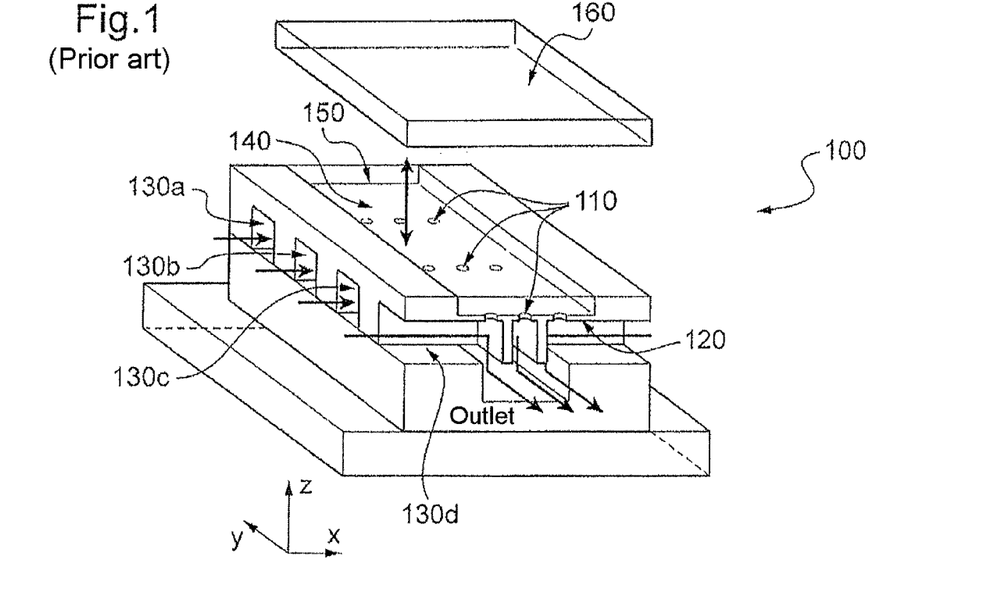
FIG. 1 is an exploded perspective view of the microfluidic device disclosed in accordance with embodiments of the invention.

The microfluidic device 100 disclosed in this document is represented in FIG. 1, in an exploded perspective view.

It comprises a PDMS structure in which are formed a number of fluid supply channels 130*a*, 130*b*, 130*c*, 130*d* that are independent of one another.

The top wall 120 of each of these channels 130*a*, 130*b*, 130*c*, 130*d* comprises one or more orifice(s) 110 passing through this wall. On the side of the wall 120 opposite the microfluidic channels, there is a culture chamber 140 for living cells filled with a culture medium 150 that takes the form of a gel, such as agarose. The wall 120 therefore forms a membrane, in as much as it makes it possible to separate two environments, namely the microfluidic channels 130*a*, 130*b*, 130*c*, 130*d*, in which a fluid is intended to circulate, and the culture chamber 140.

A glass plate 160 is used to seal the culture chamber 140, in its top part.

The fluid supply means are not represented. It must however be noted that one or more fluid(s) can be introduced into each of the channels 130*a*, 130*b*, 130*c*, 130*d*, these fluids comprising molecules intended to stimulate the living cells, by passing through the PDMS wall 120 via the diffusion orifices 110.

To control the culture of the living cells in space, it is possible, with the microfluidic device 100, to choose the channels into which a fluid comprising molecules for stimulating the living cells is sent. It is thus possible to choose with precision the orifices 110 from which these molecules will diffuse into the culture chamber 140.

Moreover, to control the culture of the living cells in time, it is possible to stagger the fluid supply for the different channels 130*a*, 130*b*, 130*c*, 130*d* in time.

The device 100 also offers a high degree of flexibility in the choice of the stimulation molecules that can be used, in as much as each of the fluid supply channels 130*a*, 130*b*, 130*c*, 130*d* provides a supply means that is specific to it.

This microfluidic system does, however, present a number of drawbacks.

It requires the use of a culture chamber 140 comprising a culture medium 150 in the form of a gel to avoid the passage of the fluid from the fluid supply channels to the culture chamber.

In this particular case, the device actually manufactured and tested has square orifices of 20 μm×20 μm. These dimensions are relatively large and favor the passage of the fluid to the culture chamber 140.

The authors stipulate that square orifices 110 of smaller dimensions, for example of 4 μm×4 μm, could be envisaged. That said, the fabrication technique employed (DRIE) is known not to allow for the formation of orifices below a maximum aspect ratio, typically 1:20, this aspect ratio here being defined by the ratio between the dimensions of the side of the orifice to the depth of this orifice. For a given dimension of the side of an orifice 110, this maximum aspect ratio limits the depth of the orifice and therefore the hydraulic resistance that this orifice can confer. The risk of the passage of fluid from a channel 130*a*, 130*b*, 130*c*, 130*d* to the culture chamber 140 is therefore increased.

Whatever the size of the orifices, it will therefore be understood that the fluid would pass to the culture chamber 140 in the absence of a culture medium 150 in the form of a gel.

It should also be noted that the essential presence of the gel brings drawbacks in the operation of the microfluidic device 100.

In fact, the gel slows down the diffusion of stimulation molecules to the targeted living cells. Thus, the stabilization of the concentration map of these stimulation molecules in the culture chamber 140 is slow.

Furthermore, it should be noted that the stimulation molecules diffuse in all directions in the gel.

Consequently, for each orifice 110 taken independently of the others, the stimulation molecules spread out, at a target situated in the gel, over a larger surface area than the surface area of passage of an orifice 110 situated in the wall 120. The stimulation of the target by specific molecules is therefore less accurate than it is theoretically with a prior choice for the dimensioning of the orifices. On the target, there is therefore a loss of spatial resolution, compared to the spatial resolution theoretically provided by the dimensions of an orifice.

Furthermore, it should be noted that the diffusion orifices 110 exhibit a certain surface density on the surface of the wall 120, which is difficult to increase. In the particular case in point, the distance between two adjacent orifices produced in the PDMS wall 120 is between 300 μm and 400 μm.

Now, the density of the orifices 110 likely to be obtained with the fabrication method employed in this article is limited. In practice, the DRIE method employed in this article to fabricate the microfluidic device exhibits limits regarding the density of the microfluidic channels that can be obtained. Since each of these microfluidic channels ends, by design, on a single orifice 110, the result thereof is that the surface density of the orifices 110 is consequently also limited.

This drawback is added to the fact that the accuracy of the stimulation of a target theoretically provided by the dimensions of an orifice is not that which is actually obtained on the target.

One objective of the invention is to mitigate at least one of these drawbacks.

To achieve this objective, the invention proposes a microfluidic system for controlling a concentration map of molecules likely to stimulate a target, for example formed by a set of living cells, characterized in that the system comprises:

a microfluidic device comprising:

$n_C \geq 1$ microfluidic channel(s), the or each channel being provided with at least one inlet orifice for at least one fluid and at least one outlet orifice for this fluid;

$n_O \geq 2$ openings formed in the microfluidic channel or distributed in the different microfluidic channels, said openings being arranged in one and the same plane so that they form a network in this plane, the numbers $n_C$ of microfluidic channel(s) and $n_O$ of openings being linked by the relationship $n_O = \Sigma_{i=1}^{n_C} n_{O/C_i}$ with $1 \leq i \leq n_C$ and $n_{O/C_i}$ the number of openings for the channel $C_i$ (the term $\Sigma$ corresponds to the "sum" operator);

at least one microporous membrane covering the network of openings, the target being intended to be arranged on the side of the membrane which is opposite the microfluidic channel(s);

one or more means for supplying fluids for supplying the or each microfluidic channel with fluid, at least one of these fluids comprising molecules for stimulating the target.

The system will be able to provide other technical features, taken alone or in combination:

the microporous membrane is provided with pores with a hydraulic diameter of between 0.05 μm and 12 μm, preferably between 0.05 μm and 3 μm;

the surface density of the pores of the microporous membrane is between $10^3$ and $10^{10}$ pores/cm$^2$;

the microporous membrane is made of a material chosen from: glass, polycarbonate, polyester, polyethyleneterephthalate, quartz, silicon, silica or silicon carbide;

a cover is provided for the microfluidic channels, said cover being made of a material chosen from: glass or silicon, a non-elastomer photo-crosslinked polymer, a metal, an electrically conductive or semiconductive alloy, a ceramic, quartz, sapphire, an elastomer;

said at least one inlet orifice and said at least one outlet orifice for the fluids are formed in the cover;

the microfluidic channels each comprise at least one wall of photo-cured and/or heat cured resin;

a closed culture chamber is provided for said target, or a microfluidic channel, arranged on the side of the microporous membrane which is opposite the microfluidic channel(s), the target thus being situated in the chamber or said one other microfluidic channel;

the chamber or the microfluidic channel comprises a base made of an optically transparent material, this base being arranged on the other side of the chamber or of the microfluidic channel relative to the microporous membrane;

the chamber or the microfluidic channel comprises lateral walls made of photo-cured and/or heat cured resin;

a plurality of means are provided for supplying the microfluidic channels, each of these supply means supplying one of the microfluidic channels;

an optical viewing means is provided;

the optical viewing means implements a photoactivation localization microscopy technique or a stimulated-emission-depletion microscopy technique;

the openings form a two-dimensional network in the plane to which they belong;

the respective centers of two adjacent openings are separated by a distance of between 10 μm and 250 μm.

Other features, aims and advantages of the invention will emerge from the following detailed description, given with reference to the following figures:

FIGS. 3(*a*) to 3(*d*) represent, according to the case, steps of a method for fabricating the microfluidic device represented in FIG. 2 or intermediate structures obtained on completion of certain steps of this method;

FIGS. 4(*a*) to 4(*c*) represent intermediate structures obtained during the fabrication of an assembly formed by a base and lateral walls of the device, said assembly being intended to form a part of the microfluidic device of FIG. 2;

FIG. 5(*a*) represents fluids flowing in the microfluidic channels of the microfluidic device according to the invention represented in FIG. 2, one of these fluids comprising stimulation molecules for the target cells and FIG. 5(*b*) represents a concentration profile of stimulation molecules in a chamber of the device of FIG. 2;

FIGS. 7(*a*), 7(*b*), 7'(*a*), 7'(*b*) and 7(*c*) to 7(*f*) represent steps in the fabrication of the microfluidic device of FIG. 6 or intermediate structures obtained in the fabrication of this microfluidic device;

FIGS. 12(a) to 12(d) represent, according to the case, steps of a method for fabricating a variant embodiment of a microfluidic device conforming to the invention or intermediate structures obtained on completion of certain steps of this method.

Figure 2:
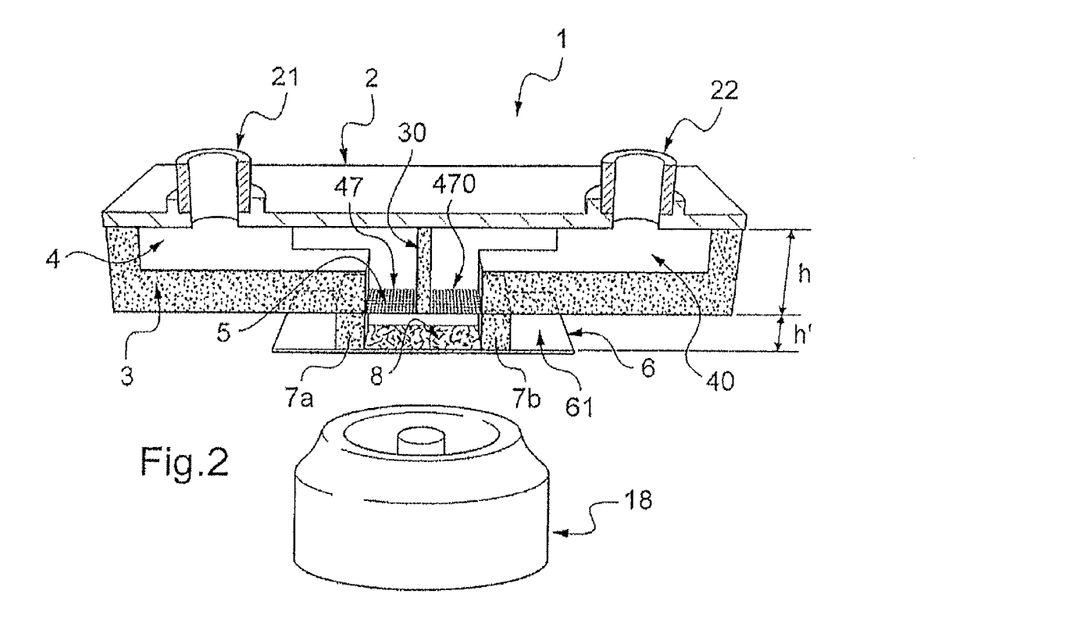
FIG. 2 is a diagram of a microfluidic system conforming to the invention, according to a partially cross-section perspective view.

First of all, we present, in support of FIG. 2, a microfluidic device 1 conforming to the invention comprising two microfluidic channels, each of these channels being provided with openings that open onto the membrane, as well as its fabrication method in support of FIGS. 3(a) to 3(d) and 4(a) to 4(c).

This microfluidic device 1 comprises a cover 2, advantageously rigid, provided with orifices 21, 22 for the circulation of fluids in microfluidic channels, a lateral wall 3 and a central wall 30, both advantageously made of photo-cured and/or heat cured resin. In particular, the lateral wall 3 of the device 1 is produced in a single layer of photo-cured and/or heat cured resin.

The microfluidic device 1 also comprises, in its bottom part, two openings 47, 470 covered by a microporous membrane 5 extending transversely to the base of the lateral wall 3 and of the central wall 30. The term opening 47, 470 should be understood to mean the end surface of the channel which extends between the walls of the device and which is intended to be covered by the membrane 5.

The openings 47, 470 are arranged in one and the same plane and can be likened to a network of openings, in this case one-dimensional, in this plane. In the context of the invention, the term "network" of openings simply describes the fact that there are a plurality of openings, without there necessarily being a link between these openings and/or a specific arrangement of these openings in the plane to which they belong.

For example, in FIG. 1, the openings 47, 470 are supplied by two different microfluidic channels, necessarily arranged in line in one and the same plane. On the other hand, in other embodiments which are described hereinbelow, some openings may be supplied by one and the same channel, the openings being, moreover, arranged in two dimensions in one and the same plane.

The walls 3, 30 and the cover 2 make it possible to define two microfluidic channels 4, 40, closed at their respective openings 47, 470 by the microporous membrane 5. The fluid inlet for each of these channels 4, 40 corresponds respectively to the orifice 21 or 22. The fluid outlets for these microfluidic channels are not represented.

The microporous membrane 5 separates two environments, namely the microfluidic channel and the external environment of this channel, this external environment being, for example, formed by a culture chamber 8 in which the target to be stimulated is intended to be arranged. In this respect, it should be noted that the gel employed in the article by Smith & al. is not a membrane, because it does not separate the microfluidic channel and the culture chamber, but, on the contrary, forms a culture medium filling the culture chamber.

Furthermore, the microporous membrane 5 prevents the fluid intended to flow in the microfluidic channels 4, 40 from passing to the other side of this membrane, the latter, however, allowing the molecules likely to stimulate the target, which are likely to be transported by the fluid in at least one of the microfluidic channels 4, 40, to diffuse, as will be detailed hereinbelow in the description. The device 1 according to the invention does not require the presence of a gel in the culture chamber 8.

The microfluidic device 1 also comprises a base 6, advantageously rigid and transparent, and lateral walls 7a, 7b, advantageously made of photo-cured and/or heat cured resin. These lateral walls 7a, 7b, the base 6 and the microporous membrane make it possible to form the chamber 8. To form the chamber 8, four lateral walls are provided, these walls being able in reality to be likened to a single outline, because the fabrication method advantageously produces these walls in a single piece.

The bottom of the chamber 8 is formed by the top face 61 of the base 6, which is intended to receive the target, for example formed by living cells. In this case, the living cells are intended to be arranged away from the microporous membrane 5, on the base 6 of the chamber 8. They can thus be cultivated in standard conditions, separately from the microfluidic device 1.

The microfluidic channels 4, 40 make it possible to circulate a fluid comprising molecules likely to stimulate the target. This is done, as will be explained in more detail hereinbelow in the description, by diffusion through the microporous membrane 5 to the chamber 8, then by diffusion through the chamber 8 (culture chamber) at the bottom of which there are, for example, living cells (CV) requiring stimulation.

Advantageously, the base 6 is made of an optically transparent material, for example glass. This is interesting, because it is then possible to arrange an optical viewing means 18 outside the device to view, for example, the response to a stimulation of the living cells arranged at the bottom of the chamber 8.

The cover 2 can be made of a material chosen from: glass or silicon, a non-elastomer photo-crosslinked polymer, a metal, an electrically conductive or semiconductive alloy, a ceramic, quartz, sapphire, an elastomer.

The microporous membrane 5 is chosen to avoid any passage of fluid between the microfluidic channels 4, 40 and the chamber 8. In reality, the microporous membrane 5 cannot be totally fluid-tight. Also, it can be considered that the cells situated in the chamber 8 are not subjected to any flow if the speed of passage of the fluid through the microporous membrane 5 is below a limit value.

This limit speed can, for example, be considered to be of the order 1 µm/s. In this case, the shearing stresses applied to the cells are negligible.

Moreover, the speed in each microfluidic channel 4, 40 can be between 100 µm/s and 10 000 µm/s, even higher than 10 000 µm/s.

Also, to obtain the limit value of 1 µm/s, the hydraulic resistance $R_{h,membrane}$ of the microporous membrane 5 should be, depending on the speed of the fluid in the channel 4, 40, 100 to 10 000 times greater than the hydraulic resistance $R_{h,channel}$ of the microfluidic channel 4, 40.

For example, if the speed of flow of the fluid in the microfluidic channel 4, 40 is 10 000 µm/s, then the following inequality must be observed:

$$10\,000 * R_{h,channel} < R_{h,membrane} \quad (R1)$$

to ensure that the speed of the fluid through the membrane 5 is well below the considered limit value of 1 µm/s.

Moreover, taking a rectangular microfluidic channel 4, 40 of height h, width w and length L, and a microporous membrane 5 of thickness e and having identical and cylindrical pores of radius $r_{pore}$, with a pore surface density ρ, then the relation (R1) is written in the form:

$$10\,000 * \mu \cdot L/(w \cdot h^3) < \mu \cdot e/(r_{pore}^4 \cdot \rho \cdot Lw) \quad (R2)$$

or:

$$\theta = r_{pore}^4 \cdot \rho/e < 10^{-4} * h^3/L^2 \quad (R3)$$

For a microfluidic channel 4, 40 of height h=100 μm, width w=1 000 μm and length L=1 000 μm, then the term θ must be less than $10^{-10}$ m to observe the relationship (R3). Furthermore, assuming cylindrical pores with a radius of 1 μm and a membrane thickness of 10 μm, the pore surface density ρ must be less than $10^5$ pores/cm$^2$.

The relationship (R3) can of course be generalized according to the considered value of the limit speed of the fluid passing through the microporous membrane 5, on the one hand, and the speed of flow of this fluid in the microfluidic channel 4, 40, on the other hand.

The microporous membrane 5 will be able to have pores with a hydraulic diameter of between 0.05 μm and 12 μm. In particular, if the pore is cylindrical, the hydraulic diameter of the pore corresponds to its diameter.

Advantageously, this hydraulic diameter will, however, be between 0.05 μm and 3 μm. In practice, it should be noted that the use of a membrane with pores with a hydraulic diameter of less than 3 μm will avoid any passage of flow into the chamber 8, for most of the conditions of use that are likely to be encountered.

Currently, the membrane manufacturers are offering on the market membranes with a hydraulic pore diameter generally greater than 0.2 μm. In the context of the invention, the pores will therefore be able to have hydraulic diameters advantageously between 0.2 μm and 3 μm. However, there is, in theory, no lower limit for the hydraulic diameter of the pores, which explains why implementing pores with a hydraulic diameter of as little as 0.05 μm can be envisaged.

If pores with a hydraulic diameter greater than 3 μm are used, the use of the microfluidic device is a priori more difficult (for example in the choice of the flow rates in the microfluidic channel 4, 40) to ensure that the fluid does not pass through the microporous membrane 5. It should however be noted that the increase in this hydraulic diameter is accompanied by a reduction in the number of pores of the membrane associated with each of the openings 47, 470 covered by the membrane 5. Now, this reduction in the number of pores of the membrane per opening favors increasing the hydraulic resistance through each opening of the microfluidic device.

For this reason, the use of pores with a hydraulic diameter greater than 3 μm can be envisaged by limiting the range of fluid flow rates that can be envisaged in the microfluidic channels.

In the device of Smith & al., an opening mandatorily corresponds to one, and only one, diffusion orifice, because there is no membrane as proposed in the invention. Consequently, the hydraulic resistance depends on the diameter of the orifice itself in the device of Smith & al.

The implementation of a microporous membrane 5 therefore offers a real advantage, since it makes it possible to dispense with a gel and the attendant drawbacks thereof.

The density of the pores of the microporous membrane 5 can, for its part, be between $10^3$ and $10^{10}$ pores/cm$^2$. The height of the pores can be between 50 nm and 100 μm.

Moreover, the microporous membrane 5 can be made from various materials such as glass, quartz, silicon, silica or silicon carbide or even polymers of the same nature as the polymers likely to be employed in the rest of the microfluidic device. It is thus possible to employ polycarbonate, polyester or polyethyleneterephthalate.

According to a first example, a microporous membrane 5 of polycarbonate can be provided, with a pore diameter of between 0.2 μm and 1 μm, for example of cyclopore type from the company Whatman (Whatman Cyclopore™). According to a second example, a microporous membrane 5 of polyester can be provided, with a pore diameter of between 0.4 μm and 3 μm, for example of Transwell type from the company Corning (Corning® Transwel®). According to a third example, a microporous membrane 5 of polyethyleneterephthalate can be provided, with a pore diameter of between 0.4 μm and 8 μm, for example of "Track-Etched" type from the company Becton Dickinson.

These microporous membranes offer the advantage of being compatible with a method for fabricating the microfluidic device 1, which is described hereinbelow with reference to FIGS. 3(a) to 3(d). They also offer the advantage of being biocompatible and functionalizable to be specifically permeable to a variety of molecules. The term functionalizable should be understood to mean that the microporous membrane 5 can be chemically modified to fulfill a particular function (retention of certain species, chemical reactions, etc.).

Generally, the device will be able to have the following dimensions. The height h of the microfluidic channel can be between 1 μm and 1 000 μm, advantageously between 10 μm and 200 μm. Its width (not represented) can be between 10 μm and 2 mm. The height h' of the chamber 8 can be between 10 μm and 1 000 μm, advantageously between 50 μm and 200 μm. Moreover, the distance between the inlet E and the outlet S is a few centimeters.

An optical viewing means 18 can be associated with the microfluidic device, as mentioned previously. This optical viewing means 18 makes it possible to know the concentration map of the stimulating molecules applied to the target cells. It also makes it possible to produce a functional imaging of the biological response of the cells to the stimulation molecules. It is therefore much easier to experimentally perform correlations between the observed behavior of the target cells and the concentration map which is applied to them.

This observation can be performed with high spatial resolution because the base made of optically transparent material can be very thin. For example, fluorescence microscopy of high resolution, even of super-resolution, can be performed with techniques such as photo-activated localized microscopy (PALM) or stimulated-emission-depletion (STED) microscopy, by using, for example, a base formed with a glass slide 150 μm thick.

Figure 3A:
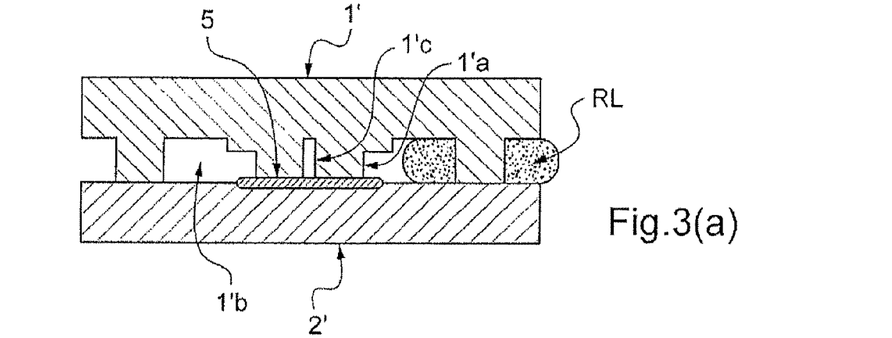
Figure 3B:
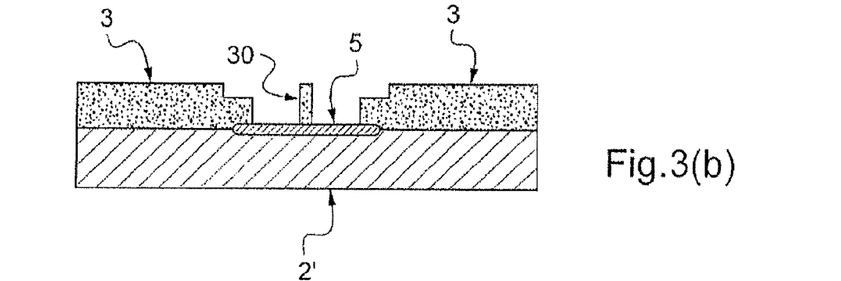
Figure 3C:
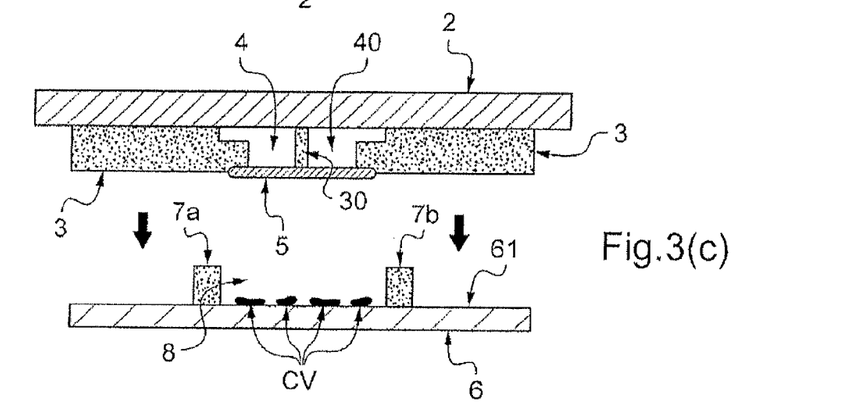
Figure 3D:
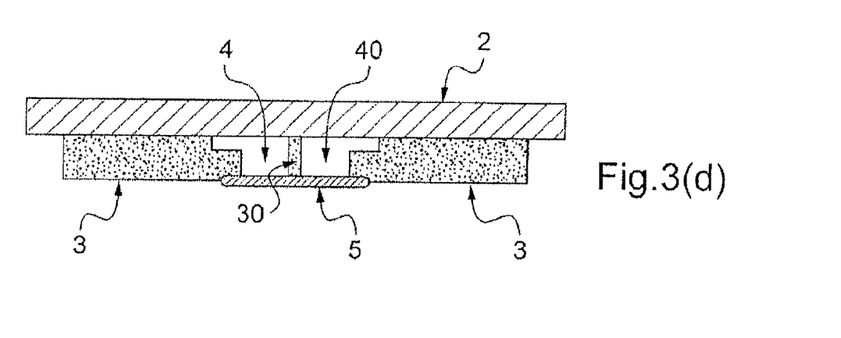

One example of a method for fabricating the microfluidic device 1 according to the invention is a method which comprises at least the steps of:

(a) using a stamp 1' made of an elastomer material to imprint a photo-curable and/or heat-curable liquid placed on a support 2' provided with the microporous membrane 5;

(b) photo-irradiating and/or heating the liquid to form, on the one hand, a first lateral wall 3 closed at its base by the microporous membrane 5 and, on the other hand, a central wall 30 in contact with the membrane 5;

(c) gluing the cover 2 provided with orifices (not represented) onto the first lateral wall 3 and onto the central wall 30, on the side opposite the support 2' to form microfluidic channels 4, 40, in each of which a fluid can circulate;

(d) after having removed the support 2', gluing onto the parts of the first lateral wall 3 and of the central wall 30 made accessible by the removal of the support 2', an assembly comprising at least the base 6 and said at least two second lateral walls 7a, 7b made of photo-cured and/or heat cured resin, to form the chamber 8.

This method is based on the method disclosed in the document WO 2008/009803.

The operation performed in the step (a) is represented in FIG. 3(a).

The stamp 1' used in the step (a) can be made of an elastomer material such as PDMS. It comprises a profile used as a mold complementing that of the microfluidic device 1 that is to be produced. The stamp 1' thus has a protuberance 1'a provided with a vertical slot 1'c to form the central wall 30 of the microfluidic device 1 that is to be obtained. It also has a hollow area 1'b surrounding the protuberance 1'a, an area in which said first lateral wall 3 of the microfluidic device 1 is intended to be formed. The support 2' can also be made of PDMS and has a flat profile.

The microporous membrane 5 is first arranged on the support 2', then the stamp 1' is pressed against the support 2'. The stamp 1' thus jams the membrane 5 against the support 2' via the protuberance 1'a.

Then, the volume situated between the stamp 1' and the support 2' is filled in an appropriate quantity, notably in the hollow area 1'b of the stamp 1' and in the slot produced in the protuberance 1'a, for example with the photo-crosslinkable and/or photo-polymerizable resin in liquid form RL. This filling does not modify the position of the microporous membrane 5, because the latter is immobilized between the stamp 1' and the support 2'.

The photo-crosslinkable and/or photo-polymerizable resin is a solution or a dispersion based on monomers and/or prepolymers. The method of the invention uses photo-crosslinkable and/or photo-polymerizable resins that are usually used as adhesives, glues or surface coatings.

Advantageously, adhesives, glues or surface coatings will be chosen that are usually employed in the optical domain. Such resins, when they have been irradiated and photo-crosslinked and/or photo-polymerized, become solid. Preferably, the duly formed solid is transparent, without bubbles or any other irregularity.

Such resins are generally based on monomers/comonomers/pre-polymers of epoxy, epoxy silane, acrylate, methacrylate, acrylic acid, methacrylic acid type, but resins such as thiolene, polyurethane and urethane acrylate can also be cited. The resins can be replaced by photo-crosslinkable aqueous gels such as polyacrylamide gels and they are chosen to be liquid at ambient temperature. The resins can also be replaced by polydimethylsiloxane (PDMS).

Among the photo-crosslinkable resins that can be used in the present invention, products that can be cited are those marketed by the company Norland Optics under the brand name NOA® Norland Optical Adhesives, such as, for example, the products NOA81 and NOA60, the products marketed by the company Dymax in the "Dymax Adhesive and light curing systems" range, the products marketed by the company Bohle in the "UV adhesives" range, the products marketed by the company Sartomer under the marketing references SR492 and SR499.

The polymerization and/or the cross-linking of these resins is performed by photo-activation using any appropriate means, such as an irradiation by UV, visible, IR radiations.

A resin will preferentially be chosen that, once polymerized and/or crosslinked, is rigid and non-flexible, because the elastomer resins have a tendency to deform when fluids are made to circulate under pressure in the microfluidic device 1. However, for certain applications, such as studying the elasticity of living cells, the use of photo-crosslinkable elastomer resins is not excluded.

After the volume situated between the stamp 1' and the support 2' has been filled with the liquid resin RL, a pressure P is then applied to the stamp 1' to drive out any excess resin. In FIG. 2, the protruding parts, and notably the protuberance 1' a of the stamp 1' made of elastomer are in contact with the support 2'. The liquid resin takes the shape of the hollow areas of the stamp 1'.

The structure obtained on completion of the step (b) is represented in FIG. 3(b).

In the step (b), the irradiation of the resin is done in the axis perpendicular to the base of the device, through the stamp 1'. The irradiation must be dosed in such a way, if so desired, as to leave on the surface of the first lateral wall 3 and of the central wall 30 made of resins, active polymerization and/or cross-linkage sites. Then, the stamp 1' is removed from the device. FIG. 3(b) shows the first lateral wall 3 made of photo-polymerized and/or photo-crosslinked resin, with a profile complementing that of the hollow areas of the stamp 1'. In this same figure, the central wall 30 can also be seen, which makes it possible to separate the microfluidic channels 4, 40.

The imprinting using a stamp 1' made of elastomer in a resin in the liquid state makes it possible to obtain structures of very small sizes with very good resolution.

Then, in the step (c), the cover 2 comprising orifices for the circulation of fluid in the microfluidic channels 4, 40, is fixed on the side of said first lateral wall 3 previously in contact with the stamp 1'. The support 2' can then be removed. The structure obtained on completion of the step (c) is represented in FIG. 3(c), without the orifices of the cover, which are situated in another plane.

The removal of the support 2' is performed without the microporous membrane being unglued from the photo-polymerized and/or photo-crosslinked resin, and without it being torn away or partially torn.

The cover 2 can be produced with glass, silicon, a solid polymer film, a metal, a conductive or semiconductive alloy, a ceramic, quartz, sapphire, an elastomer.

Preferably, a glass slide, a polymer film or a silicon slide will be chosen. The materials used to form the cover 2 are chosen according to the application which will be made of the microfluidic device 1.

Thus, a cover 2 made of optically transparent material, such as glass, is more appropriate to facilitate observation and optical detection (transparency). Another advantage of glass is its very good heat conductivity which makes it possible to perform a uniform heating of the devices.

It should be noted that the arrangement of the microporous membrane 5 in the bottom part of the microfluidic channel 4 makes its use compatible with the standard living cell culture protocols. In practice, it is then possible to envisage the base 6 being a glass slide on which a living cell culture is performed, this slide then being fixed to the structure obtained on the completion of the step (c) to form the chamber 8 (culture chamber), as is explained hereinbelow in the description.

It should be noted that the fabrication method described previously can make it possible to fabricate openings with dimensions reaching 5 µm, with a pitch (distance between the respective centers of two adjacent openings) between two adjacent openings that can be as small as 10 µm, and therefore notably between 10 µm and values less than 300 µm, as is mentioned in the paper by Smith & al. In particular, the pitch can be between 10 µm and 250 µm.

Figures 4A, 4B, 4C:
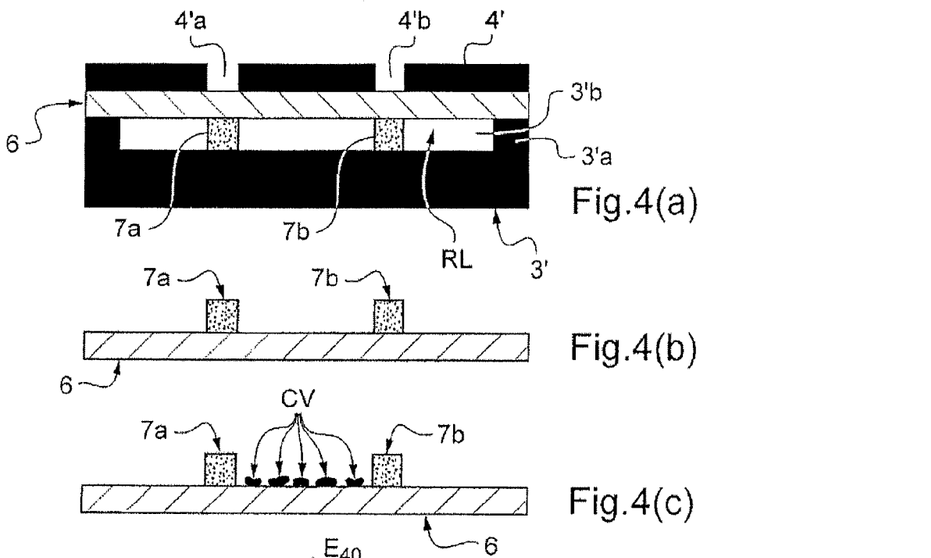

The assembly comprising a base 6 and two second lateral walls 7a, 7b can be produced from the following steps of the method:

($e_1$) using an open mold 3' made of elastomer material having a support face 3'a and a cavity 3'b intended to receive a photo-curable and/or heat-curable liquid resin RL;

($e_2$) positioning the base 6 on the support face 3'a of the mold 3';

($e_3$) positioning a mask 4' on the base 6, then photo-irradiating or heating to form said second lateral walls 7a, 7b.

The structure obtained on completion of the steps ($e_1$) to ($e_3$) is represented in FIG. 4(a), in the case where the step ($e_3$) consists of a photo-irradiation of the liquid resin.

The mold 3', like the stamp 1' and the support 2', can be made of an elastomer such as PDMS.

The photo-curable and/or heat-curable liquid resin used for these steps can be chosen from the possibilities already described for the liquid resin employed in the step (a). Preferably, the liquid resins employed for the steps (a) and ($e_1$) to ($e_3$) are the same. As a variant, photo-crosslinkable aqueous gels could be used, such as those described previously, or polydimethylsiloxane (PDMS).

The base 6 can be chosen from the materials employed for the cover. Advantageously, an optically transparent material will be able to be used to facilitate optical viewing by a dedicated device. This optically transparent material can notably be glass, the base 6 thus forming a glass cover usually used for the culture of living cells (CV). The use of glass moreover makes it possible to exploit the chemical and biological surface treatments that exists for this substrate.

The mask 4' can have orifices 4'a, 4'b making it possible to photo-irradiate precise areas of the liquid resin in order to form said second lateral walls 7a, 7b of the microfluidic device.

Once the step ($e_3$) is finished, all that remains is to remove the mask 4' and the mold 3' in a step ($e_4$) to leave only the assembly formed by said second lateral walls 7a, 7b and the base 6. This assembly is represented in FIG. 4(b).

Generally, a step ($e_5$) is then performed, the latter consisting in rinsing said assembly, for example using an ethanol/acetone mixture in proportions by volume of 90/10. This rinsing makes it possible to remove all the resin not photo-irradiated or not heated that is likely to remain on the base 6.

Then, a culture of living cells (CV) is performed before this assembly is arranged with the structure obtained on completion of the step (c) and before beginning the step (d).

For this, this assembly must be biocompatible.

To this end, this assembly can be strongly photo-irradiated, for example by UV, followed by a vigorous rinsing in a neutral solution, such as water, for several hours.

As a variant, it is possible to fabricate the chambers, or more generally the various elements of the device, with biocompatible materials.

Finally, a culture of living cells can then be performed on the top face 61 of the base 6, as represented in FIG. 4(c). This culture is performed in standard conditions. In particular, this culture can be performed on a base 6 in the form of a conventional glass slide.

Once this culture is finished, the step (d) can be carried out.

The operation performed during the step (d) is represented in FIG. 3(d).

Once the step (d) has been carried out, the microfluidic device 1 is ready for use. It comprises notably living cells on the top face 61 of the base 6, which is opposite to the microporous membrane 5 in the chamber 8 (culture chamber).

In order to operate the microfluidic device 1, the latter is associated, in a microfluidic system, with at least one means for supplying at least one of the microfluidic channels 4, 40 with a fluid comprising molecules likely to stimulate a target, such as living cells.

For example, two independent fluid reservoirs can be provided, one to supply the microfluidic channel 4 with a fluid $F_1$ comprising stimulation molecules for the target, the other for supplying the second microfluidic channel 40 with a neutral fluid $F_2$.

Figures 5A, 5B:
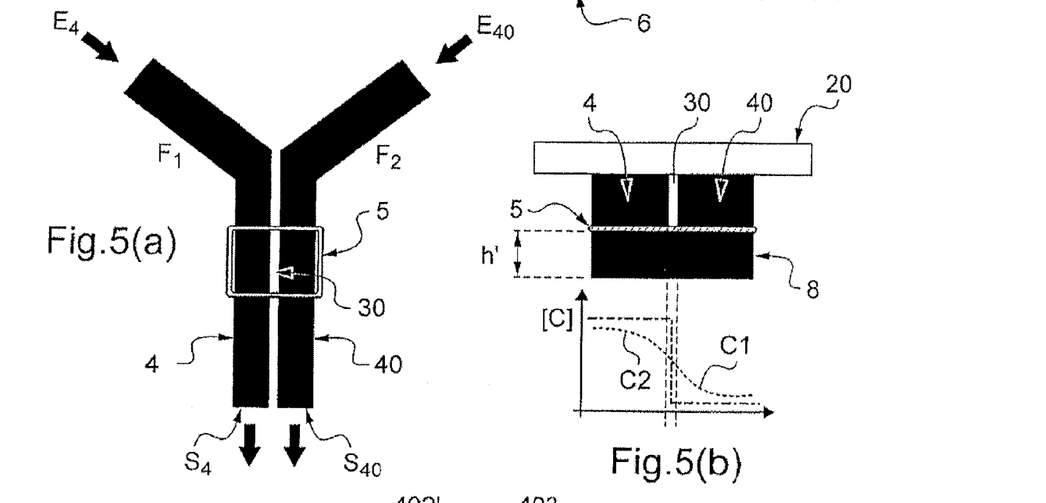

An example of microfluidic channels 4, 40 likely to be used with these reservoirs is schematically represented in FIG. 5(a), in a plan view.

The fluid $F_1$ is introduced into the microfluidic channel 4 through the inlet $E_4$, and emerges from this channel 4 through the outlet $S_4$. The fluid $F_2$, for its part, is introduced into the microfluidic channel 40 through the inlet $E_{40}$, and emerges from this channel 40 through the outlet $S_{40}$. The two microfluidic channels 4, 40 are, of course, separated by the central wall 30 of the microfluidic device 1.

The separation provided by the central wall 30 makes it possible to recycle the fluids circulating in each of the microfluidic channels 4, 40, because no mixing can take place between these fluids. Furthermore, by virtue of this separation, the speeds of flow of the fluids can extend within a wide range of values, for example between 100 μm/s and 10 000 μm/s, even more, without risking any hydrodynamic mixing of the two fluids under the effect of shear forces. Furthermore, a difference of speed of circulation of the fluids between the different channels can be envisaged without this causing any problem in operating the device.

The fluids $F_1$, $F_2$ differ only by the presence, in one of the two fluids and in weak concentration, of stimulation molecules for the target cells.

It should be noted that the inlets $E_4$, $E_{40}$ are comparable to the inlet orifices 21, 22 of FIG. 2.

FIG. 5(b) schematically represents the flow of the fluids $F_1$, $F_2$ in the different parts of the microfluidic device, which is schematically represented from a vertical cross-sectional view.

Each fluid $F_1$, $F_2$ is therefore intended to flow in one of the microfluidic channels 4, 40 of the microfluidic device 1, both in contact with the microporous membrane 5, but not in the chamber 8 (culture chamber). The concentration map of these molecules in the channels 4, 40 is represented by the staircase-form curve C1.

The transport of the molecules (contained in the fluid $F_1$) likely to stimulate the living cells, between the microfluidic channel 4 and said cells installed on the base 6 of the chamber 8, is then performed by diffusion in the chamber 8, through the microporous membrane 5.

More specifically, the transport of these molecules is performed firstly by diffusion through the microporous membrane 5, then by diffusion through the chamber 8, to finally reach the top face 61 of the base 6 of the chamber 8, the face 61 on which the living cells are situated.

The concentration map must then be stabilized in the chamber 8. In particular, at the base 6 of the chamber 8, the stabilization time $t_{stab}$ is of the order of $h'^2/D$ where h' is the height of the chamber 8 and D the diffusion coefficient of the molecules intended to stimulate the target cells in the chamber 8. It should be noted that, to avoid excessively long stabilization times, the height of the chamber will generally be limited to 500 μm.

The concentration map thus stabilized in the chamber 8 is represented by the curve C2, which is in the form of a curve representative of a function of "erf" type. With this supply of the microfluidic channels, it is therefore possible to obtain a quite particular concentration map at the base of the chamber 8, and therefore on the living cells that are to be stimulated.

The supply described above in support of FIGS. 5(a) and 5(b) is only one example given as an illustration. Thus, the supply of fluid to the microfluidic channels could be performed differently in order to obtain other types of concentration maps on the target cells.

Thus, according to another example, a supply means could be provided that makes it possible to supply each of the two microfluidic channels 4, 40 with the fluids $F_1$ and $F_2$, in order to obtain more complex concentration maps in the chamber 8.

The closed chamber 8 can be replaced by a microfluidic channel comprising orifices, advantageously lateral, although no fluid is then intended to flow in this microfluidic channel when a test is in progress. However, channels can be connected to the lateral orifices to recover the secretions from the living cells, in order to analyze them chemically. Moreover, between two tests, a rapid rinsing or a change of culture medium can then be envisaged.

Moreover, it should be noted that it would also be possible to arrange the target cells not on the base of the chamber 8 or of the microfluidic channel, but on the microporous membrane 5 itself. In such a case, the concentration map obtained on the target cells corresponds to the concentration map generated in the microfluidic channels 4, 40. In practice, in this case, the target cells are situated on the side of the membrane 5 which is opposite to the side in contact with the fluids which flow in the microfluidic channels 4, 40.

Moreover, it is even possible to fabricate a microfluidic device 1 without chamber or without microfluidic channel, the target cells being placed directly on the microporous membrane 5. In this case, it will be understood that the steps ($e_1$) to ($e_3$) described previously are not required to fabricate the device.

Another microfluidic device conforming to the invention will now be described in support of FIGS. 6 and 8, as well as a method for fabricating this device in support of FIGS. 7(a), 7(b), 7'(a), 7'(b) and 7(c) to 7(f).

Figure 6:
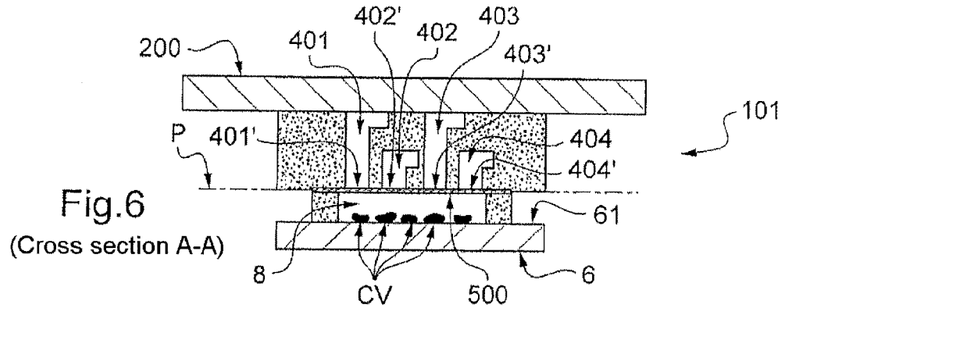
FIG. 6 represents another microfluidic device conforming to the invention, according to a cross-sectional view.
Figure 7:
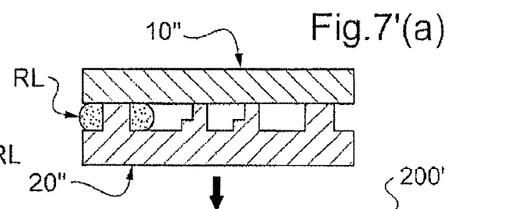
Figure 7A:
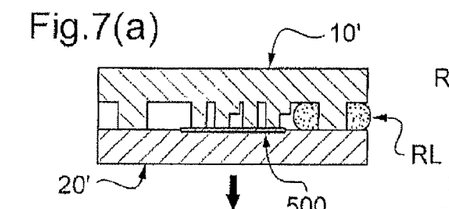

The microfluidic device 101 represented in FIG. 6 comprises a number of microfluidic channels 401, 402 each comprising several openings 401', 402' on the one hand and 403', 404' on the other hand which open onto the microporous membrane 500. In this case, two microfluidic channels are provided, supplying, for one 401, the six openings represented in white in FIG. 8 and, for the other 402, the six openings represented in black in this FIG. 8. These openings 401', 402', 403', 404' are arranged in one and the same plane P so as to form a network of openings which is two-dimensional in this plane. The plane P is represented in FIG. 6 and in FIG. 8, the latter representing said openings as seen from below at the level of this plane P.

The microporous membrane 500 extends transversely relative to the lateral walls of the different microfluidic channels in order to cover the different channels in their bottom parts and therefore cover the different openings.

Advantageously, the microporous membrane 500 covers all of said openings 401', 402', 403', 404' of the microfluidic channels 401, 402. That makes it possible to cover the different openings with a single membrane, which is particularly practical when the network of openings is dense. Typically, the method according to the invention can make it possible to fabricate openings of 5 μm, separated from one another by a pitch of 10 μm. The pitch is here defined as the distance separating the respective centers of two adjacent openings.

The microporous membrane 500 is provided with pores. The characteristics of this membrane 500 can be the same as the membrane 5 of the microfluidic device 1 described previously supported by FIGS. 2, 3(a) to 3(d) and 4(a) to 4(c).

The microfluidic device 101 also comprises a cover 200 for the microfluidic channels. This cover 200 can be made of a material chosen from: glass or silicon, a non-elastomer photocrosslinked polymer, a metal, an electrically conductive or semi-conductive alloy, a ceramic, quartz, sapphire, an elastomer.

The inlet and outlet orifices for the fluids intended to circulate in the microfluidic channels 401, 402 can be formed in this cover 200 (not represented).

The hydraulic diameter of the pores of the microporous membrane 500 prevents the fluids flowing in the microfluidic channels 401, 402 from passing through this membrane 500, only the molecules likely to stimulate the target passing through it. In this respect, reference should be made to the relationships (R1) to (R3) supplied previously and to the choice of the limit speed below which the membrane is considered not to allow the fluid flowing in the microfluidic channels 401, 402 to pass.

The concentration map of these stimulation molecules is then generated by the choice of the fluid supply for each of the different microfluidic channels 401, 402. As can be seen in the representation of FIG. 8 (the microporous membrane 500 is not represented), the openings 401', 402', 403', 404' that open onto the microporous membrane 500 form diffusion areas for the stimulation molecules, that can be likened to pixels supplying chemical information to the target.

The microfluidic device 101 advantageously provides a closed culture chamber 8 for said target. This chamber is thus arranged on the side of the microporous membrane 500 which is opposite to the first microfluidic channels 401, 402. The chamber has characteristics similar to those of the chamber 8 of the microfluidic device 1 described previously, but its dimensions have to be adapted.

Thus, the microporous membrane 500 extends transversely between the lateral walls of the chamber to close said chamber in its top part.

The target can be positioned on the base 61 of the chamber 8, a base 61 which is positioned on the other side of the chamber 8, relative to the microporous membrane 500.

As a variant, it is perfectly possible to envisage positioning the target in the chamber 8, directly on the microporous membrane 500, even positioning the target directly on the microporous membrane, in the absence of any chamber.

There again, the culture chamber 8 can be replaced by a microfluidic channel comprising orifices, advantageously lateral, but with no fluid being intended to flow in this channel.

An optical viewing means such as the means 18 described previously and represented in FIG. 2 can also be associated with the microfluidic device 101, particularly if the base of the chamber 8 or of the microfluidic channel is optically transparent.

The method for fabricating the microfluidic device 101 is based on steps similar to the steps (a) to (d) described previously for the microfluidic device represented in FIG. 2, by adapting it.

Figure 7B:
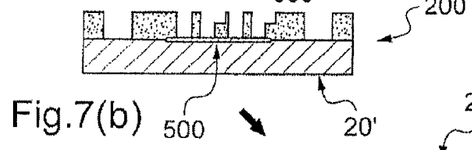

The steps (a) and (b) are thus implemented to produce the structure 200 represented in FIG. 7(b). In the step (a), the stamp 10' made of an elastomer material is therefore used to imprint a photo-curable and/or heat-curable liquid RL placed on a support 20' provided with the microporous membrane 500 (FIG. 7(a)). Then, in the step (b), a photo-irradiation and/or a heating of the liquid is performed to form several walls with the microporous membrane 500.

Similarly, the steps (a) and (b) are implemented to produce another structure 200' represented in FIG. 7'(b). More specifically, in the step (a), the stamp 10" made of an elastomer material is used to imprint a photo-curable and/or heat-curable liquid RL placed on a support 20", in the absence of any microporous membrane (FIG. 7'(a)). Then, in the step (b), a photo-irradiation and/or a heating of the liquid is performed to form several walls.

Figure 7C:
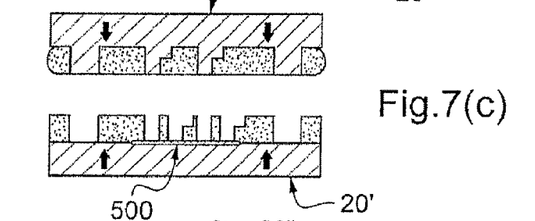

Then, the structures 200', 200" which have been produced independently of one another are joined to one another, through a new photo-irradiation or a new heating. This makes it possible to create a permanent bond between the liquid resins of the structures 200' and 200" (FIG. 7(*c*)).

Figure 7D:
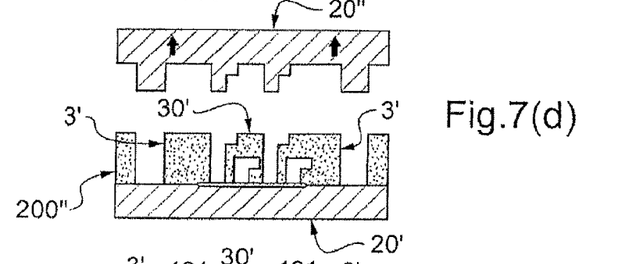

Once the structures have been assembled, one 20" of the supports 20', 20" is removed to reveal a new structure 200" formed by the assembly of the structures 200, 200'. Then, a step reprising the step (c) described previously is carried out. In other words, a cover 200 provided with orifices (not represented) is thus glued onto the different walls 3', 30' of the structure 200", on the side opposite the microporous membrane 500, to form the microfluidic channels 401, 402.

Figure 7E:
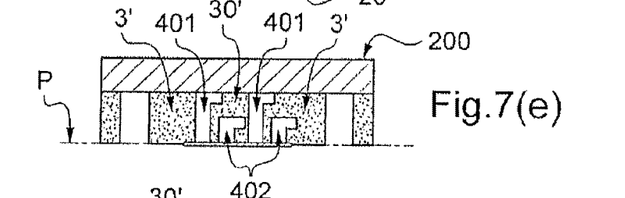
Figure 7F:
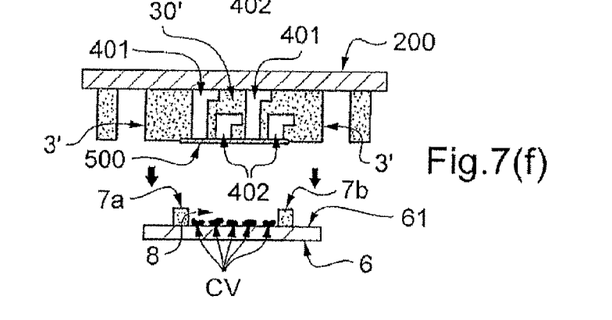
Figure 9:
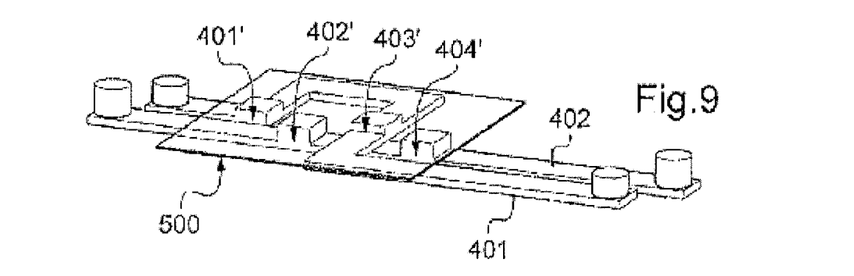
FIG. 9 represents, according to a perspective view, microfluidic channels of the microfluidic device of FIG. 6, arranged in such a way that each microfluidic channel comprises a number of openings.

The support 20' in contact with the microporous membrane 500 is then removed (FIG. 7(*e*)). In this FIG. 7(*e*), the microfluidic channels 401, 402 are shown. It will be noted that the microfluidic channel 401 on the one hand, and the microfluidic channel 402 on the other hand, have different depths which makes it possible to superpose the channels in a plane, as can be seen in FIG. 9.

Then, an assembly comprising at least the base 6 and said at least two second lateral walls 7*a*, 7*b* made of photo-cured and/or heat cured resin is glued onto the membrane 500, in accordance with the step (d) described previously, to form the chamber 8. This assembly, for its part, is fabricated with a method reprising the steps (e₁) to (e₃) described previously supported by FIGS. 4(*a*) to 4(*c*).

It should be noted that the walls of the microfluidic channels 401, 402 of the microfluidic device 101 that is thus obtained, as well as the walls of the chamber 8 of this device, can be produced with resins as described previously or, as a variant, with photo-crosslinkable aqueous gels, such as polyacrylamide gels, chosen to be liquid at ambient temperature. The resins can also be replaced by polydimethylsiloxane (PDMS).

To operate the microfluidic device 101 of FIG. 6, the latter is associated, in a microfluidic system, with at least one means for supplying at least one of the microfluidic channels 401, 402 with a fluid comprising molecules likely to stimulate a target, such as living cells.

For example, a specific supply means (not represented), such as a fluid reservoir, can be provided for each microfluidic channel 401, 402. The connection between the reservoir and the associated microfluidic channel can be made by a capillary.

Figure 8:
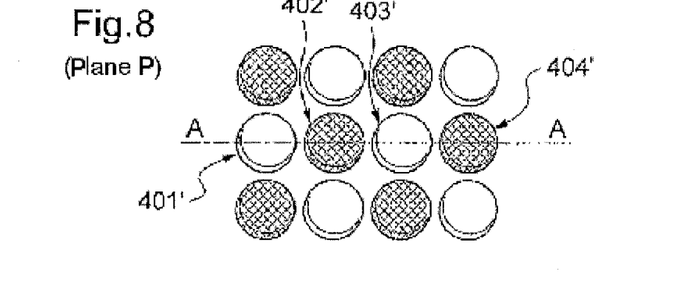
FIG. 8 is a diagram representing the microfluidic device of FIG. 6, according to a partial view from below.

The microfluidic channels 401, 402 are schematically represented in FIG. 9, according to a partial perspective view which represents only the channels 401, 402 supplying the openings 401', 402', 403', 404' according to the cross-sectional view A-A of FIG. 8, a cross section which also corresponds to the view chosen to describe the fabrication method supported by FIGS. 7(*a*) to 7(*f*), 7'(*a*) and 7'(*b*).

The arrangement represented in FIG. 9 makes it possible to run parallel experiments with a reduced number of connection systems, in as much as one supply will make it possible to supply a number of openings.

However, the arrangement of the microfluidic channel can be different, by retaining a two-dimensional network of openings as is represented in FIG. 8.

Figure 10:
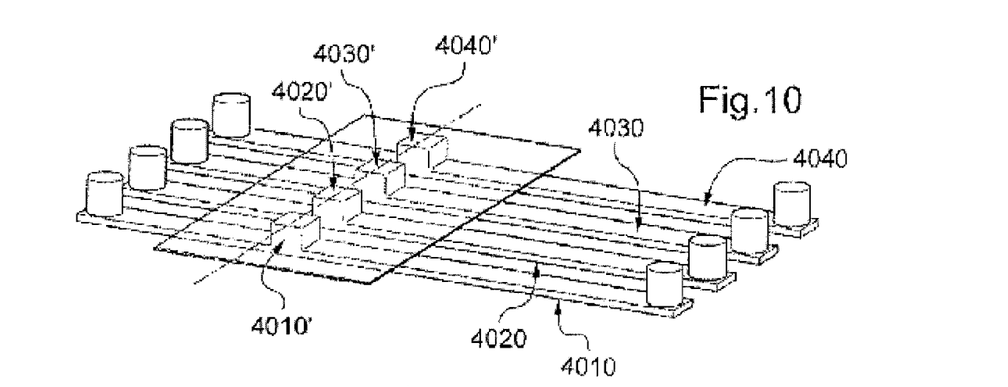
FIG. 10 represents, according to a view from above, microfluidic channels of a microfluidic device according to a variant of FIG. 6, these channels being arranged in such a way that each microfluidic channel comprises an opening that opens onto a microporous membrane of this device.

Thus, it is possible to envisage each channel comprising only a single opening, so that there are as many channels as openings. Such a case is represented in FIG. 10, which represents only four channels 4010, 4020, 4030, 4040 (respectively associated with an opening 4010', 4020', 4030', 4040') out of the twelve microfluidic channels associated with the twelve openings of FIG. 8. In this FIG. 10, each microfluidic channel can be supplied with a dedicated fluid, that can notably comprise molecules for stimulating the target.

The supply of each channel is thus independent. Moreover, it can then be modulated at the inlet by valves making it possible to have at least two fluids pass in succession into the channel.

The duly formed microfluidic device is therefore a device comparable to the device described with the support of FIG. 2. However, it comprises more than two microfluidic channels.

In these conditions, it will be understood that the method for fabricating such a device will reprise the fabrication steps described with the support of FIGS. 3(*a*) to 3(*c*) and, where appropriate, the step described with the support of FIGS. 3(*d*), 4(*a*) to 4(*c*) to form a chamber or another microfluidic channel.

Figure 11:
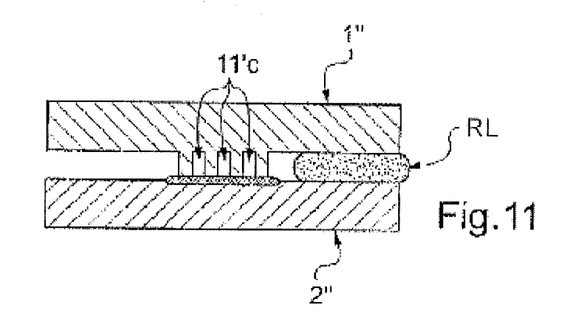
FIG. 11 represents a step in the fabrication of the device represented in FIG. 10.

To this end, the shape of the stamp 1' must, however, be modified in order for the protuberance 1'*a* to include, in place of the vertical slot 1'*c*, a hollow area in grid form suitable for forming the walls separating the microfluidic channels from one another, to ultimately obtain the network of openings of FIG. 8. FIG. 11 shows the duly modified stamp 11' comprising this hollow area in grid form 11'*c* on the protuberance with the support 2", in the step corresponding to the step represented in FIG. 3(*a*).

This offers numerous possibilities.

In practice, it is possible to choose the microfluidic channels to supply with fluid, according to the desired concentration map of molecules likely to stimulate the target.

It is also possible to supply microfluidic channels with different types of molecules stimulating the target. In this way, an accurate and varied control in the space of the living cell culture can be performed.

For example, it is possible to supply one microfluidic channel with a fluid comprising stimulation molecules and another microfluidic channel, for example immediately adjacent to the first microfluidic channel, with a fluid comprising a neutral solution. The fluids are then mixed in the chamber 8 to form a quite particular concentration map at the base of the chamber, when the target cells are situated on this base.

It is also possible to stimulate the target through the desired opening 401', 402', 403', 404' with a time offset from one microfluidic channel 401, 402, 403, 404 to the other. The other openings represented in FIG. 8 can also be supplied in the same way.

Another arrangement of the microfluidic channels that can be envisaged is as follows.

It is in fact possible to provide only a single microfluidic channel in which circulates a fluid comprising stimulation molecules for the target, this channel comprising a number of openings.

For example, the fabrication of a device comprising one channel with four openings may be required, with the microfluidic channel therefore supplying fluid to these four openings.

A method for fabricating such a device is presented supported by FIGS. 12(*a*) to 12(*d*), in the case where a chamber 8 is also provided (FIG. 12(*d*)).

Figure 12A:
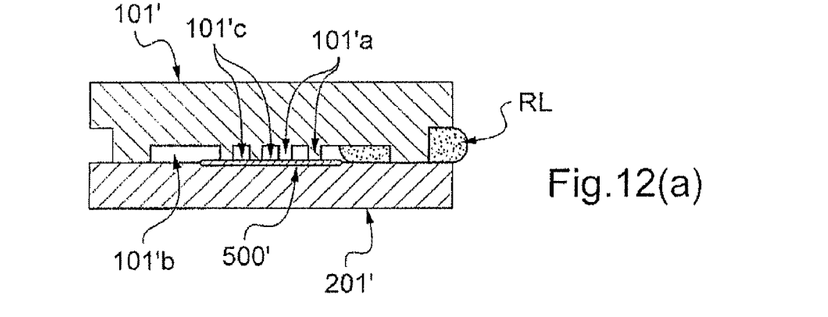

The stamp 101' can be made of an elastomer material such as PDMS. It comprises a profile used as mold complementing that of the microfluidic device that is to be produced. The stamp 101' thus comprises a protuberance 101'*a* provided with a number of vertical slots 101'*c* to form the different walls 301' of the microfluidic device. It also comprises a hollow area 101'*b* surrounding the protuberance 101'*a*, an area in which the lateral wall 300' of the microfluidic device is intended to be formed. The support 201' can also be made of PDMS and has a flat profile.

The microporous membrane 500' is first arranged on the support 201', then the stamp 101' is pressed against the support 201'.

Then, the volume situated between the stamp 101' and the support 201' is filled with an appropriate quantity, for example with photo-crosslinkable and/or photo-polymerizable resin in liquid form RL. After the volume situated between the stamp 101' and the support 201' has been filled with the liquid resin RL, a pressure P is then applied to the stamp 101' to drive out any excess resin.

The structure obtained on completion of step (b) is represented in FIG. 3(b).

Figure 12B:
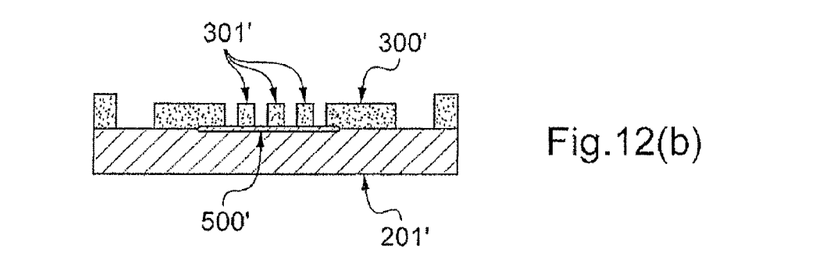

The resin is irradiated through the stamp 101'. Then, the stamp 101' is removed from the device. In FIG. 12(b) the walls 300', 301' of photo-polymerized and/or photo-crosslinked resin can be seen, with profiles complementing the hollow areas of the stamp 101'.

The cover 200' is then fixed, on the side of said first lateral wall 300' previously in contact with the stamp 101'. The support 201' can then be removed. The structure obtained on completion of this step is represented in FIG. 12(c).

Figure 12C:
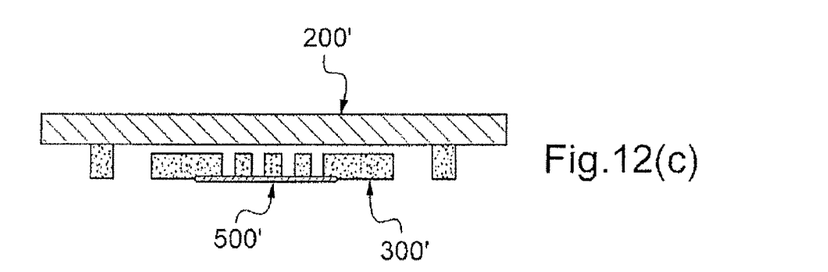

The chamber 8 is fabricated according to the method previously described supported by FIGS. 4(a) to 4(c), then assembled with the structure represented in FIG. 12(c). This assembly operation is represented in FIG. 12(d).

Figure 12D:
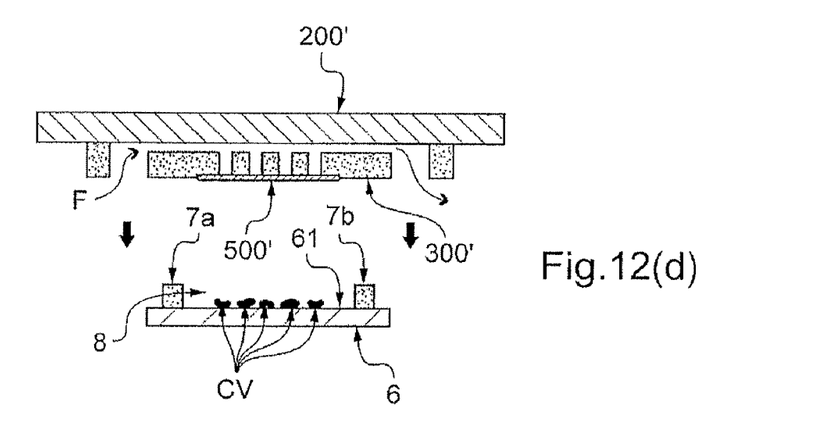

The direction of travel of the fluid in the channel is denoted F in FIG. 12(d). It will be noted that it supplies in succession the different openings opening onto the membrane 500'.

Here again, the different materials already presented previously can be envisaged. The presence of the chamber 8 is not mandatory, a channel notably being able to be provided in place of this chamber 8. The membrane 500' will have the same characteristics as the membranes 5, 500 described previously.

The invention thus implements a membrane in which the hydraulic diameter of the pores is shrewdly chosen to avoid the passage of the fluid from the microfluidic channels to the opposite side of the membrane, comprising, for example, the chamber or another microfluidic channel. The hydraulic diameter of the pores can, moreover, extend over a wide range. The invention does not therefore require any culture medium in gel form to avoid the passage of fluid from the microfluidic channels to the chamber or this other microfluidic channel.

The diffusion in the culture chamber is therefore performed in a liquid culture medium, such as water. This diffusion in the chamber is therefore faster than in a culture medium produced with a gel. This makes it possible to perform a test more rapidly and also to run different tests in sequence more rapidly.

Moreover, the accuracy with which stimulation molecules reach a target that is obtained with the device according to the invention is excellent, and much better than with the known devices.

This is notably linked to the absence of gel in the chamber, which limits the multidirectional diffusion of the stimulation molecules observed with this gel.

Furthermore, the method according to the invention makes it possible to fabricate a network of openings of small dimensions, with a high surface density. Typically, the dimension of the openings can reach 5 μm and the distance between the respective centers of two adjacent openings can reach 10 μm.

Finally, the dimensioning of the openings is totally independent of the hydraulic diameter of the pores of the microporous membrane. Thus, it is possible to fabricate a microfluidic device with small openings (size of 30 microns or less for example), associated with a microporous membrane that has large pores (3 microns for example). It is also possible to fabricate a microfluidic device with large openings (size of 2000 microns for example), associated with a microporous membrane 500 having small pores (0.2 micron for example).

This allows a wide degree of freedom of choice in the dimensioning of the microfluidic device, according to the application envisaged.

The invention is particularly applicable in the field of biology, for the culture, observation and study of living cells. In particular, it is possible to determine the chemotactical response of nerve cells to certain molecules, for example in order to create neural networks. Also in particular, it is possible to measure the response of cancer cells to molecules employed for chemotherapy. It is also possible to use the microfluidic system for fabricating biochips or for the stimulation of tissues, notably for producing artificial tissues.

The advantages linked to the invention may be of interest for other fields of application, for example for determining toxicity thresholds of certain molecules in cosmetology.

The invention claimed is:

1. A microfluidic system comprising:
   a microfluidic device comprising:
   $n_c > 1$ microfluidic channel(s), the or each channel being provided with at least one inlet orifice for at least one fluid and at least one outlet orifice for this fluid;
   $n_0 > 2$ openings formed in the microfluidic channel or distributed in the different microfluidic channels, said openings being arranged in one and the same plane so that they form a network in this plane,
   the numbers $n_c$ of microfluidic channel(s) and $n_0$ of openings being linked by the relationship $n_0 = \Sigma_{i=1}^{n_c} n_{O/C_i}$ with $1 \leq i \leq n_c$ and $n_{O/C_i}$ the number of openings for the channel $C_i$;
   a chamber or another microfluidic channel comprising a base configured to receive a target, wherein the target is formed by a set of living cells;
   at least one microporous membrane covering the network of openings, the base configured to receive the target being arranged on the other side of the chamber or of the other microfluidic channel, relative to the microporous membrane; and
   one or more means for supplying fluids for supplying the or each microfluidic channel with fluid, at least one of these fluids comprising molecules for stimulating the target,
   wherein said microporous membrane is impervious to said fluids and adapted to allow said molecules to diffuse therethrough so that, when the supply means supplies the microfluidic channel or each microfluidic channel with at least one of these fluids, diffusion of the molecules likely to stimulate the target occurs, after having passed through the microporous membrane, through the chamber or said one other microfluidic channel; and
   wherein after the diffusion of the molecules likely to stimulate the target, a concentration map of the molecules likely to stimulate the target in the chamber or the other microfluidic channel is generated.

2. The microfluidic system as claimed in claim 1, in which the microporous membrane is provided with pores with a hydraulic diameter of between 0.05 μm and 12 μm.

3. The microfluidic system as claimed in claim 2, in which the surface density of the pores of the microporous membrane is between $10^3$ and $10^{10}$ pores/cm$^2$.

4. The microfluidic system as claimed in claim 1, in which the microporous membrane is made of a material chosen from: glass, polycarbonate, polyester, polyethyleneterephthalate, quartz, silicon, silica or silicon carbide.

5. The microfluidic system as claimed in claim 1, in which a cover is provided for the microfluidic channels, said cover being made of a material chosen from: glass or silicon, a non-elastomer photo-crosslinked polymer, a metal, an electrically conductive or semiconductive alloy, a ceramic, quartz, sapphire, an elastomer.

6. The microfluidic system as claimed in claim 5, in which said at least one inlet orifice and said at least one outlet orifice for the fluids are formed in the cover.

7. The microfluidic system as claimed in claim 1, in which the microfluidic channels each comprise at least one wall of photo-cured and/or heat cured resin.

8. The microfluidic system as claimed in claim 7, in which the base of the chamber or of the other microfluidic channel is made of an optically transparent material.

9. The microfluidic system as claimed in claim 8, in which the chamber or the microfluidic channel comprises lateral walls made of photo-cured and/or heat cured resin.

10. The microfluidic system as claimed in claim 1, in which a plurality of means are provided for supplying the microfluidic channels, each of these supply means supplying one of the microfluidic channels.

11. The microfluidic system as claimed in claim 1, in which an optical viewing means is provided.

12. The microfluidic system as claimed in claim 11, in which the optical viewing means implements a photoactivation localization microscopy technique or a stimulated-emission-depletion microscopy technique.

13. The microfluidic system as claimed in claim 1, in which the openings form a two-dimensional network in the plane to which they belong.

14. The microfluidic system as claimed in claim 1, in which the respective centers of two adjacent openings are separated by a distance of between 10 μm and 250 μm.

15. The microfluidic system as claimed in claim 1, in which the microfluidic channels have openings that are separated by a central wall that is perpendicular to the microporous membrane and to a top cover of the microfluidic system.

16. The microfluidic system according to claim 14, wherein the fluids only differ by the presence of stimulation molecules.

17. The microfluidic system as claimed in claim 1, in which at least one of the microfluidic channel is supplied independently of the other channels in the case where the number $n_c$ of microfluidic channel is higher or equal to 2.

18. A method for controlling a concentration map of molecules likely to stimulate a target comprising:
provide a microfluidic system as claimed in claim 1;
placing a target formed by a set of living cells on the base of said chamber or said other microfluidic channel;
supplying the or each microfluidic channel with fluids, at least one of these fluids comprising molecules for stimulating the target;
wherein, when the fluids are supplied, diffusion of molecules likely to stimulate the target occurs, after going through the microporous membrane, through said chamber or said other microfluidic channel; and
wherein, after the diffusion of the molecules likely to stimulate the target, a concentration map of the molecules likely to stimulate the target in the chamber or the other microfluidic channel is generated.

* * * * *